United States Patent [19]
Suryadevara

[11] Patent Number: 5,871,502
[45] Date of Patent: Feb. 16, 1999

[54] PROCESS FOR MANUFACTURING A POLYPROPYLENE MONOFILAMENT SUTURE

[75] Inventor: Jogendra Suryadevara, Cedar Knolls, N.J.

[73] Assignee: Ethicon, Inc., Somerville, N.J.

[21] Appl. No.: 629,152

[22] Filed: Apr. 8, 1996

[51] Int. Cl.⁶ ................................................. A61B 17/04
[52] U.S. Cl. ................ 606/228; 606/230; 606/231; 264/210
[58] Field of Search ............................. 606/228, 230, 606/231; 254/210.8, 289.6, 290.5

[56] References Cited

U.S. PATENT DOCUMENTS

| | | | |
|---|---|---|---|
| 3,048,467 | 8/1962 | Roberts et al. | 18/54 |
| 3,092,891 | 6/1963 | Baratti | 28/82 |
| 3,106,442 | 10/1963 | Compostella et al. | 18/48 |
| 3,152,380 | 10/1964 | Martin | 28/72 |
| 3,161,709 | 12/1964 | Noether et al. | 264/210 |
| 3,215,486 | 11/1965 | Hada et al. | 8/74 |
| 3,256,258 | 6/1966 | Herrman | 260/93.7 |
| 3,323,190 | 6/1967 | Boltniew | 28/72 |
| 3,330,897 | 7/1967 | Tessier | 264/176 |
| 3,359,983 | 12/1967 | Northey | 128/335.5 |
| 3,413,397 | 11/1968 | Bierbaum et al. | 264/290 |
| 3,432,590 | 3/1969 | Papps | 264/210 |
| 3,549,743 | 12/1970 | Riordon | 264/290 |
| 3,630,205 | 12/1971 | Listner | 128/335.5 |
| 3,636,956 | 1/1972 | Schneider | 128/335.5 |
| 3,739,056 | 6/1973 | Evans et al. | 264/290 |
| 4,520,822 | 6/1985 | Menezes et al. | 128/335.5 |
| 4,557,264 | 12/1985 | Hinsch | 128/335.5 |
| 4,578,451 | 3/1986 | Weaver et al. | 528/292 |
| 4,620,542 | 11/1986 | Menezes et al. | 128/335.5 |
| 4,621,638 | 11/1986 | Silvestrini | 128/335.5 |
| 4,671,280 | 6/1987 | Dorband et al. | 128/334 |
| 4,911,165 | 3/1990 | Lennard et al. | 606/231 |
| 4,970,038 | 11/1990 | Stanko | 264/130 |
| 5,217,485 | 6/1993 | Liu et al. | 606/228 |
| 5,236,444 | 8/1993 | Muth et al. | 606/230 |
| 5,269,807 | 12/1993 | Liu | 606/228 |
| 5,294,395 | 3/1994 | Broyer | 264/178 F |
| 5,405,358 | 4/1995 | Liu et al. | 606/231 |
| 5,587,122 | 12/1996 | Lennard | 264/178 F |
| 5,626,811 | 5/1997 | Liu | 264/210.7 |

FOREIGN PATENT DOCUMENTS

| | | |
|---|---|---|
| 0 415 783 A2 | 3/1991 | European Pat. Off. . |
| 0 526 759 A1 | 2/1993 | European Pat. Off. . |

OTHER PUBLICATIONS

"Physical Aging of Drawn Polypropylene Fibers"— C.P. Buckley and M. Habibullah, Univ. of Manchester Institute of Science and Technology. Journal of Applied Polymer Science, vol. 26, pp. 2613–2623 (1981).

"Aging Phenomena in Isotactic Polypropylene Drawn at Different Temperatures" F. de Candia, R. Russo, A. Tidjani, V. Vittoria and A. Peterlin, Istituto di Richerche su Tecnologia dei Polimeri e Reologia, Napoli Italy. Journal of Polymer Science: Part B: Polymer Physics, vol. 26, pp. 1897–1906 (1988).

The mechanical behaviour and physical ageing of semicrystalline polymers: 2 L.C.E. Struik, Plastics and Rubber Research Institute TNO, 1987 Butterworth & Co. 1534–Polymer. 1987, vol. 28, Aug.

The mechanical and physical ageing of semicrystalline polymers: 1—L.C.E. Struik, (Same as Above) accepted Apr. 7, 1987.

Mechanical behavior and physical ageing of semi–crystalline polymers: 3 Prediction of long term creep form short time tests, L.C.E. Struik, accepted Nov. 1, 1988.

Mechanical Behavior and Physical Ageing of Semi–Crystalline Polymers: 4 L.C.E. Struik accepted Nov. 1, 1988.

Primary Examiner—Michael Buiz
Assistant Examiner—Tina T.D. Pham
Attorney, Agent, or Firm—Hal Brent Woodrow

[57] ABSTRACT

The present invention provides an improved process for manufacturing a polypropylene monofilament suture comprising aging a polypropylene filament that has been drawn in two separate drawing steps in the range of from about 4xto about 8.5xfor less than two days then annealing the polypropylene filament to provide a polypropylene suture.

9 Claims, 1 Drawing Sheet

PROCESS FOR MANUFACTURING A POLYPROPYLENE MONOFILAMENT SUTURE

FIELD OF THE INVENTION

This invention relates to a process for making polypropylene surgical filaments.

BACKGROUND OF THE INVENTION

Surgical sutures made from polypropylene have been successfully used by the medical profession for more than twenty years. One of the first commercially successful polypropylene suture to gain wide acceptance was described in U.S. Pat. No. 3,630,205 to Gregory J. Listner. Listner disclosed a process for manufacturing polypropylene suture that comprised the steps of drawing an extruded polypropylene suture to about 6.6 times its original extruded length in a single step and then relaxing or shrinking the monofilament to between about 91 to 76 percent of the stretched length.

Others have described sutures fabricated from polypropylene homopolymers and copolymers and from polymer blends containing polypropylene have also been described in U.S. Pat. Nos. 3,359,983, 4,520,822, 4,557,264, 4,620,542, 4,621,638 and 4,911,165.

Recently issued U.S. Pat. No. 5,217,485 describes a process for making polypropylene suture consisting of extruding, stretching (orienting), permitting the monofilament to equilibrate (age) for a period of at least 2 days prior to annealing the monofilament. The process described in the U.S. Pat. No. 5,217,485 (except for the specific storage time) is similar to the process single step draw process described in U.S. Pat. No. 3,630,205. The improvement supposedly obtained by this process was a reduced 0–5% and 0–10% strain energies, however, the data present in the patent do not support this conclusion. The strain energy exhibited by a fiber is indicative of the processing conditions used to manufacturing the fiber. Strain energy can be affected by several fiber processing steps such as the draw ratio used in orienting the fiber and any subsequent relaxation and/or annealing steps. Therefore, unless fibers with identical process histories are compared, it will be difficult to attribute decreases in strain energies to any specific factor. The U.S. Pat. No. 5,217,485 did not compare sutures with the same processing conditions, therefore, did not establish that equilibrating a suture after drawing the suture has any affect on suture properties.

It is an object of the present invention to provide an improved process for manufacturing polypropylene sutures which does not require a holding period of at least 2 days.

SUMMARY OF THE INVENTION

I have discovered a process for manufacturing a polypropylene monofilament suture comprising aging a polypropylene filament (that has been drawn in two separate drawing steps in the range of from about 4x to about 8.5x) for less than two days then annealing the polypropylene filament to provide a polypropylene suture.

BRIEF DESCRIPTION OF THE INVENTION

The FIGURE is a side elevation, partially schematic of an apparatus suitable for carrying out the process of the present invention.

DETAILED DESCRIPTION OF THE INVENTION

Figure 1:
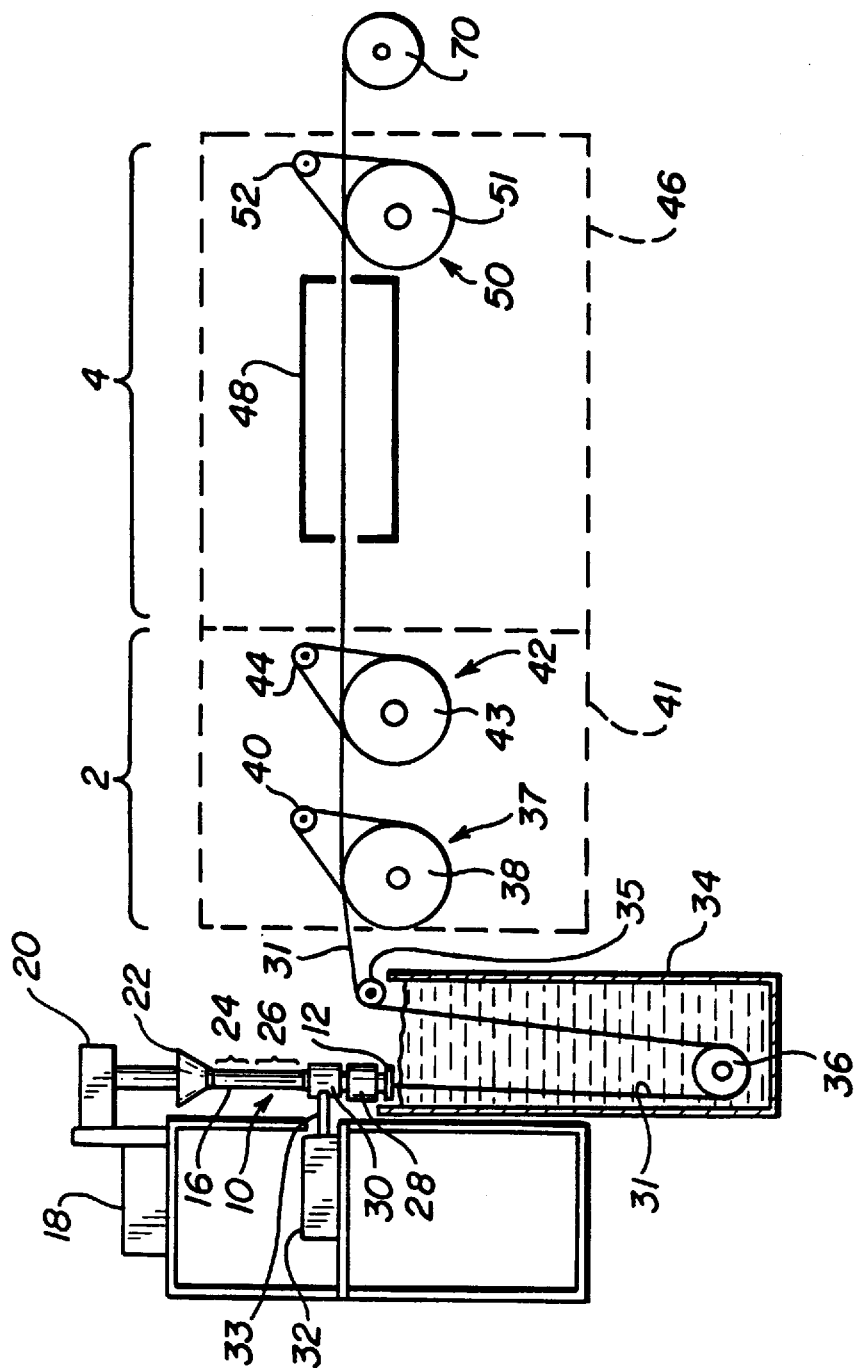

I have discovered that for a polypropylene suture that is oriented by two drawing steps there is no need to hold the suture about two days before annealing the suture. To facilitate the rapid processing of polypropylene sutures the sutures may be annealed in less than about 2 days, preferably in less than 40 hours, more preferably in the range of from about 2 to about 40 hours and most preferably in the range of from about 2 to about 36 hours. Additionally, it appears to be advantageous to anneal sutures that are drawn in two steps in less than about 2 days, because as shown in Example 3 there is a trend for longer holding periods between drawing and annealing to result in higher Young's Modulii. There also appears to be no improvement in strain energies attributable to increasing the period a fiber is held between drawing and annealing.

As used herein the term polypropylene shall include isotactic and syndiotactic polypropylene and blends thereof, as well as, blends composed predominantly of isotactic or syndiotactic polypropylene blended with heterotactic polypropylene and polyethylene (such as is described in U.S. Pat. No. 4,557,264 issued Dec. 10, 1985 assigned to Ethicon, Inc. hereby incorporated by reference) and copolymers composed predominantly of propylene and other alpha-olefins such as ethylene (which is described in U.S. Pat. No. 4,520,822 issued Jun. 4, 1985 assigned to Ethicon, hereby incorporated by reference). The preferred polypropylene material for making sutures is isotactic polypropylene without any other polymers blended or monomers copolymerized therein. The preferred method for preparing the flexible polypropylene sutures of the present invention utilizes as the raw material pellets of isotactic polypropylene homopolymer having a weight average molecular weight of from about 260,00 to about 420,000. Polypropylene of the desired grade is commercially available in both powder and pellet form.

Referring to the FIGURE, there is shown an apparatus that is suitable for carrying out the present invention. An extruder 10 (which may be horizontally or vertically extruder) is terminated at one end with an extrusion die 12. A longitudinal extruder screw is mounted for rotation within the barrel 16 and is driven by a variable speed motor 18 through a gear 20. Polypropylene pellets are introduced into the extruder through hopper 22 which communicates with the barrel 16. In normal operation of the extruder 10, the feeding zone 24 of the extruder is maintained at a temperature in the range of from about 140° C. to about 200° C., the transition zone 26 is maintained at a temperature in the range of from about 170° C. to about 220° C., and the pump block 30, block 28 and die 12 are maintained at a temperature in the range of from about 170° C. to about 225° C. A pump 33 driven by a motor 32, pumps the molten polypropylene through spinneret orifices in the die 12 to form a plurality of filaments 31 (for simplicity only one filament is shown in the FIGURE). The filament 31 is extruded into quench bath 34. The quench bath 34 is filled with a liquid heat exchange medium. The surface of the liquid in the quench bath 34 is preferably not more than a few centimeter below the die 12 in order to achieve rapid cooling of the extruded filament 31, (i.e. from in the range of from about 0.1 cm to about 20 cm). The quench bath 34 is maintained at a temperature below 50° C. and preferably the quench bath 34 is maintained at about 20° C. The filament 31 enters the quench bath 34 and travels around idler roll 36 in the quench bath 34 and then up out of the quench bath 34 to another idle roller 35 then to the first godet 37 in the first drawing zone 2. In the first drawing zone 2 the filament 31 is drawn in the range of from about 4.0 to 7.5x its original length. The filament 31 may be drawn incrementally or in several discrete steps in the first drawing zone 2. The drawing will preferably be performed in a first heated zone 41 (such as a heated cabinet, oven, or by using heated godets) and a drawing pin may be used to stabilize the drawing point. The temperature of the first heated zone will preferably be in the range of from about 30° C. to about 170° C. Most preferably the first godet will be maintained at a temperature in the range of from about 40° C. to 140° C. and the second godet will be maintained at a temperature from about 60° C. to about 82° C. The filament 31 will remain in the first heated zone 41 generally only a short time preferably in the range of from about 0.1 seconds to about 5 seconds.

In the preferred embodiment of the invention shown in the attached FIGURE, the filament 31 is drawn by a first godet 37 and a second godet 42. The first godet 37 includes a main roll 38 and an air bearing 40. The first godet 37 is rotated at a peripheral speed that is equal to or slightly higher than the speed at which the filament 31 is extruded from the die orifice 12. The first godet 37 may be combined with a pinch roller (not shown) to assure the filament 31 does not slip in the subsequent drawing to the extruded filament 31. The first draw of the extruded filament 31 will be performed by feeding the extruded filament 31 from the first godet 37 to second godet 42 which includes a main roll 43 and an air bearing 44. The second godet 42 is rotated at a peripheral speed that is in the range of from about 4.0 to about 7.5×of the speed of the first godet 37.

The filament 31 then passes into a second drawing zone 4, where the filament 31 is drawn again in the range of from about 1.0×to about 2.5×while in a second heated zone 46. The filament 31 may be drawn incrementally or in one or more discrete steps in the second drawing zone 4. The drawing will be performed in a second heated zone 46. The temperature of the second heated zone 46 will be in the range of from about 180° C. to about 280° C., preferably in the range of from about 195° C. to about 260° C. The filament 31 will remain in the second heated zone 46 generally only a short time preferably in the range of from about 0.1 seconds to about 5 seconds.

In the preferred embodiment of the invention shown in the attached FIGURE, the filament 31 passes through a second heated zone 46 to a third godet 50. The second heated zone 46 is preferably an oven 48 that is maintained at a temperature of in the range of from about 180° C. to about 280° C., preferably in the range of from about 195° C. to about 260° C. The filament 31 is drawn in the range of from about 1×to about 2.5×, while traveling from the second godet 42 to the third godet 50 in the second heated zone 46. The third godet 50 includes a main roll 51 and an air bearing 52, that are rotating at a peripheral speed of about 1×to about 2.5×of the peripheral speed of the second godet 42. Preferably the draw ratio will be in the range of from about 1.06×to about 1.9×.

The total draw ratio may range from 4×to about 8.5×. Preferably, the draw ratio will be in the range of from about 7×to 8.2×and most preferably from 7.75×to 8×.

The residence time of filament 31 within any of the heated zones can be optimized to improve fiber properties. The overall residence time that filament 31 is present in the first and second heated zones will preferably be in the range of from about 0.2 seconds to about 5 seconds. The residence time can be increased with longer ovens or by having multiple wraps of the fiber on the godets.

After the filament 31 has been drawn in accordance with the procedures described above it may be wound on a tube spool 70. It is then annealed in an oven and allowed to shrink from about 16 to about 35 percent of the original length (i.e., the final length will be from about 65 to 84 percent of the pre-shrink length). The annealing is carried out at a temperature within the range of from about 135° to about 152° C., for a period of time sufficient to permit the filament to shrink to the degree indicated above and heat set at that shrinkage. Normally, this will take from about 5 to about 40 minutes. Preferably the suture will be wound on racks as described in U.S. Pat. No. 3,630,205 Listner assigned to Ethicon, Inc. (hereby incorporated by reference). Additionally, the ovens and racks should be configured to provide uniform heating to all the filaments.

After the drawing and annealing, the filaments of the invention are fabricated into surgical sutures in accordance with customary procedures. They can be produced in the usual sizes, for example, from size 2 down to size 11/0. They can be attached to needles by the usual procedures, and can then be sterilized (as by using ethylene oxide) and package in sterile packs ready for use.

The polypropylene that is employed to produce the sterile suture of the invention can contain the usual stabilizers against heat, ultraviolet and oxidative degradation. Such stabilizers include hindered phenols, tertiary amines, and the like. The polypropylene can also contain dyes, colorants, and lubricants.

The following non-limiting examples are further provided to illustrate the practice of the present invention.

EXAMPLE 1

Dyed isotactic polypropylene having a melt flow of 3–5 as determined by ASTM D1238 was used to produce surgical sutures under the conditions set forth in Table 1 below.

TABLE 1

| Sample No. | 1 | 2 | 3 |
| --- | --- | --- | --- |
| Filament Size | 2/0 | 2/0 | 2/0 |
| Feed Zone °C. | 168 | 167 | 167 |
| Transition Zone °C. | 182 | 182 | 183 |
| Pump °C. | 186 | 186 | 187 |
| Block °C. | 186 | 186 | 186 |
| Die °C. | 190 | 190 | 190 |
| Barrel PSI | 1200 | 1200 | 1200 |
| Pump PSI | 673 | 679 | 690 |
| Die PSI | 394 | 428 | 405 |
| Pump RPM | 11.7 | 11.7 | 11.6 |
| Screw RPM | 8 | 9 | 7 |
| Godet 1 FPM/°C. | 18/118 | 18/118 | 18/118 |
| Godet 2 FPM/°C. | 104/85 | 104/85 | 104/85 |
| Orienting /Annealing Oven °C.[1] | 128.9 | 128.9 | 126.1 |
| Godet 3 FPM | 127 | 127 | 127 |

RPM is revolutions per minute.
FPM is feet per minute.
[1]The oven was approximately six (6) feet long.

RPM is revolutions per minute.
FPM is feet per minute.
[1]The oven was approximately six (6) feet long.

EXAMPLE 2

The fiber prepared in Example 1 were annealed at different times after the fibers had been extruded and drawn. The 0–5% and 0–10% strain energies of these annealed fibers were measured using Instron Model 4200 Universal Testing Instrument. The strain energy was determined by calculating the area under the stress-strain curve at 5% and 10% extension. The Instron test program was modified to perform this as a recalculation of data from pull test. The strain energy data is reported in Tables 2 and 3 below.

TABLE 2

| Sample No. | Time Held Before Annealing After Drawing Hrs. | Strain Energy 0–5% Kg-mm | | | |
|---|---|---|---|---|---|
| | | 0 | 1 | 2 | 3 |
| 1 | 0 | 2.6 | 1.9 | 2.7 | 2.6 |
| 2 | 2 | 1.7 | 1.6 | 2.4 | 2.6 |
| 3 | 4 | 1.9 | 2.0 | 2.5 | 2.6 |
| 4 | 8 | 1.7 | 2.6 | 2.5 | 2.7 |
| 5 | 12 | 1.8 | 2.6 | 2.6 | 2.8 |
| 6 | 18 | 1.7 | 2.7 | 2.7 | 2.8 |
| 7 | 24 | 1.4 | 2.7 | 2.8 | 2.8 |
| 8 | 48 | 2.2 | 2.6 | 2.8 | 2.7 |

TABLE 3

| Sample No. | Time Held Before Annealing After Drawing Hrs. | Strain Energy 0–10% Kg-mm | | | |
|---|---|---|---|---|---|
| | | 0 | 1 | 2 | 3 |
| 1 | 0 | 9.3 | 8.3 | 10.2 | 9.8 |
| 2 | 2 | 7.1 | 7.5 | 9.2 | 9.6 |
| 3 | 4 | 7.4 | 8.4 | 9.7 | 10.1 |
| 4 | 8 | 7.1 | 9.5 | 9.4 | 9.9 |
| 5 | 12 | 7.6 | 9.6 | 9.8 | 10.1 |
| 6 | 18 | 7.4 | 10.2 | 10.4 | 10.5 |
| 7 | 24 | 7.0 | 10.5 | 10.6 | 10.6 |
| 8 | 48 | 8.7 | 10.1 | 10.6 | 10.4 |

The strain energy data reported in Tables 2 and 3 indicate that there is no correlation between reduced strain energy and the time a fiber is equilibrated between drawing and annealing.

EXAMPLE 3

The fibers prepared in Example 1 were annealed at different times after the fibers had been extruded and drawn. The Young's Modulii of these annealed fibers were calculated in psi from the initial stress-strain data generated during tensile strength tests. The tensile strength test were performed on an Instron Model 4200 Universal Testing Instrument with a gauge length of 12.7 cm, a chart speed of 30.5 cm/min and a crosshead speed of 30.5 cm/min. Young's Modulus is the ratio of applied stress to strain in the elastic region of the suture and measures the elastic component of a suture's resistance to stress. This value relates to the flexibility of a suture.

TABLE 4

| Sample No. | Time Held Before Annealing After Drawing Hrs. | Young's Modulus Kpsi | | | |
|---|---|---|---|---|---|
| | | 0 | 1 | 2 | 3 |
| 1 | 0 | 237 | 289 | 320 | 316 |
| 2 | 2 | 207 | 290 | 293 | 305 |
| 3 | 4 | 218 | 274 | 334 | 324 |
| 4 | 8 | 207 | 281 | 283 | 303 |
| 5 | 12 | 220 | 290 | 317 | 296 |
| 6 | 18 | 239 | 317 | 318 | 325 |
| 7 | 24 | 222 | 337 | 331 | 327 |
| 8 | 48 | 248 | 334 | 327 | 343 |

I claim:

1. A process for manufacturing a polypropylene monofilament suture comprising (a) aging a polypropylene filament in the range of from about 2 to about 40 hours that has been drawn in two separate drawing steps in the range of from about 4x to about 8.5x (of the filament's original length) then;

(b) annealing the polypropylene filament to provide a polypropylene suture.

2. The process of claim 1 wherein the polypropylene filament that has been drawn in two separate drawing steps is drawn in the first step in the range of from about 4x to about 7.5x (of the filament's original length).

3. The process of claim 1 wherein the polypropylene filament that has been drawn in a first drawing step to form a drawn filament and in the second step is drawn in the range of from about 1.0x to about 2.5x (of the drawn filament's length).

4. The process of claim 1 wherein the polypropylene filament has been drawn in the range of from about 7x to about 8.2x (of the filament's original length).

5. The process of claim 1 wherein the polypropylene filament is aged in the range of from about 2 to about 36 hours.

6. A process for manufacturing a polypropylene monofilament suture comprising (a) aging a polypropylene filament in the range of from about 2 to about 40 hours, that has been drawn in two separate drawing steps the polypropylene filament having been drawn in the first drawings step in the range of from about 4x to about 7.5x (of the filament's original length) to form a drawn filament, and the drawn filament is drawn in the second step in the range of from about 1.06x to about 1.9x (of the drawn filament's length) then;

(b) annealing the polypropylene filament to provide a polypropylene suture.

7. The process of claim 6 wherein the polypropylene suture is allowed to shrink in the range of from about 16 to about 35 percent based on the original length of the suture.

8. The process of claim 7 wherein the polypropylene suture has been drawn in the range of from 7.75x to 8x (of the drawn filament's length).

9. The process of claim 6 wherein the polypropylene filament is aged in the range of from about 2 to about 36 hours.

* * * * *